US012642777B2

(12) United States Patent
Liu et al.

(10) Patent No.: US 12,642,777 B2
(45) Date of Patent: *Jun. 2, 2026

(54) USE OF MITOXANTRONE PREPARATION IN PREPARATION OF DRUG FOR DIAGNOSING AND TREATING BREAST CANCER

(71) Applicants: SHENZHEN CHINA RESOURCES JIUCHUANG MEDICAL AND PHARMACEUTICAL CO., LTD, Shenzhen (CN); SHENZHEN CHINA RESOURCES GOSUN PHARMACEUTICALS CO., LTD, Shenzhen (CN)

(72) Inventors: Jun Liu, Shenyang (CN); Xun Li, Shenyang (CN); Zhanao Yang, Shenzhen (CN); Feina Tu, Shenzhen (CN); Ning Chen, Shenzhen (CN); Quanhua Huang, Shenzhen (CN); Ge Pan, Shenzhen (CN); Baolin Lai, Shenzhen (CN); Weiwei Zhang, Shenzhen (CN); Yijing Hu, Shenzhen (CN); Yang Li, Shenzhen (CN)

(73) Assignees: SHENZHEN CHINA RESOURCES JIUCHUANG MEDICAL AND PHARMACEUTICAL CO., LTD, Shenzhen (CN); SHENZHEN CHINA RESOURCES GOSUN PHARMACEUTICALS CO., LTD, Shenzhen (CN)

( * ) Notice: Subject to any disclaimer, the term of this patent is extended or adjusted under 35 U.S.C. 154(b) by 470 days.

This patent is subject to a terminal disclaimer.

(21) Appl. No.: 18/018,587

(22) PCT Filed: Mar. 23, 2021

(86) PCT No.: PCT/CN2021/082262
§ 371 (c)(1),
(2) Date: Jan. 30, 2023

(87) PCT Pub. No.: WO2022/021906
PCT Pub. Date: Feb. 3, 2022

(65) Prior Publication Data
US 2023/0321009 A1 Oct. 12, 2023

(30) Foreign Application Priority Data
Jul. 29, 2020 (CN) .......................... 202010742444.8

(51) Int. Cl.
| | |
|---|---|
| *A61K 31/136* | (2006.01) |
| *A61K 9/00* | (2006.01) |
| *A61K 47/02* | (2006.01) |
| *A61K 47/12* | (2006.01) |
| *A61K 47/20* | (2006.01) |
| *A61P 35/04* | (2006.01) |

(52) U.S. Cl.
CPC .......... *A61K 31/136* (2013.01); *A61K 9/0019* (2013.01); *A61K 47/02* (2013.01); *A61K 47/12* (2013.01); *A61K 47/20* (2013.01); *A61P 35/04* (2018.01)

(58) Field of Classification Search
CPC ...... A61K 31/136; A61K 9/0019; A61P 35/04
USPC ......................................................... 514/646
See application file for complete search history.

(56) References Cited

U.S. PATENT DOCUMENTS

| | | | | |
|---|---|---|---|---|
| 12,171,864 B2 * | 12/2024 | Liu et al. | ................. | A61K 9/00 |
| 2020/0163872 A1 * | 5/2020 | Liu et al. | ................. | A61K 9/00 |

FOREIGN PATENT DOCUMENTS

| | | | | | |
|---|---|---|---|---|---|
| CN | 102397561 A | * | 4/2012 | ............. | A61K 49/00 |
| WO | WO 2018/233095 A1 * | | 12/2018 | ............... | A61K 9/08 |

OTHER PUBLICATIONS

Novantrone Package Insert, Immunex, p. 1-36. (Year: 2000).*
Baichev G, Sergieva S, Gorchev G. Sentinel lymph nodes identification in early breast cancer-peritumoral or subareolar injection of lymphotropic blue dye?. Radiology and Oncology. Mar. 1, 2001;35(1). (Year: 2001).*
Translation CN102397561A, google patents, pp. 1-12. (Year: 2012).*

* cited by examiner

*Primary Examiner* — Jeffrey S Lundgren
*Assistant Examiner* — Heather Dahlin
(74) *Attorney, Agent, or Firm* — JMB Davis Ben-David

(57) ABSTRACT

The use of a mitoxantrone preparation in the preparation of a drug for diagnosing and treating breast cancer. Provided is the use of mitoxantrone and/or a pharmaceutically acceptable salt thereof in the preparation of a lymphatic tracer in a disease associated with breast resection. No local or systemic toxic and side effects are seen after local injection of the preparation, suggesting that the preparation has good tolerance, effectiveness and safety, which provides a new treatment idea for thoroughly curing breast cancer in a breast cancer patient.

7 Claims, No Drawings

USE OF MITOXANTRONE PREPARATION IN PREPARATION OF DRUG FOR DIAGNOSING AND TREATING BREAST CANCER

CROSS-REFERENCE TO RELATED APPLICATIONS

This is the U.S. National Stage of International Patent Application No. PCT/CN2021/082262 filed on Mar. 23, 2021, which in turn claims the benefit of Chinese Patent Application No. 202010742444.8 filed on Jul. 29, 2020.

TECHNICAL FIELD

The present disclosure belongs to the field of pharmaceutical preparations, and specifically, relates to an application of mitoxantrone for lymphatic tracing in mastectomy.

BACKGROUND

Metastasis is the basic biological characteristic of malignant tumors and is also the main cause of postoperative tumor recurrence and patient death. The cure rate and survival rate of patients with malignant tumors will be significantly reduced, once they develop metastasis. Lymphatic metastasis is one of the important factors affecting the prognosis of patients with malignant tumors.

In operative treatment for patients with breast cancer, intraoperative lymphangiography and sentinel lymph node biopsy (SLNB) have attracted increasing attention, as a highly sensitive method for detecting axillary lymph node metastasis.

Sentinel lymph node (SLN) is the specific lymph nodes that firstly receive lymphatic drainage from the tumor area and develop tumor metastasis at earliest, and it receives the raw lymph fluid and the maximum drainage volume, which is most likely to contain metastatic tumor cells. SLN is the first barrier for cancer cells to metastasize through lymph. If there is no metastasis in SLN, there is little chance of metastases for other lymph nodes in this area.

At present, the exiting SLNB methods include a dye method, a nuclide method, and a dye-nuclide combined application.

The main dye-based lymph node tracers reported at home and abroad include methylene blue, nano-carbon, isosulfan blue, and patent blue, etc. At present, methylene blue and nano-carbon are more used as the lymph node tracers in clinic in China, while isosulfan blue and patent blue are less used in China due to their high prices and difficulty for purchasing in China.

Among the above-described dye-based lymph node tracers, isosulfan blue or patent blue has weak binding power to protein, and after being injected, isosulfan blue or patent blue disperses in a small amount of tissues and stains the tissues quickly. However, staining duration of isosulfan blue or patent blue is shorter, so it is necessary to repeatedly inject isosulfan blue or patent blue. Moreover, isosulfan blue and patent blue are expensive and are not produced in China. Staining duration of methylene blue is long, but methylene blue has stronger binding power to protein, so it also stains surrounding tissues blue. The dye method is an important method, and selection of an ideal dye as a lymphatic tracer is an important guarantee to further improve the success rate of SLNB. However, the currently available lymphatic tracers in China are very limited, and only nano-carbon, with the trade name Canarine, is mainly used for tracing draining lymph nodes in the gastric cancer area. Other dyes are not approved for corresponding indications, and there is no clear instruction.

Nano-carbon is in an accumulated state in vivo and is not metabolized in vivo. When entering the blood and lymph circulation, it may block capillaries. Moreover, if the texture of cancer tissues is harder and more brittle, direct intratumor injecting of the nano-carbon may cause necrosis and falling off of tumor tissues to cause bleeding.

The nuclide method can accurately position lymph nodes, and is easy to perform in an operation, however, a special detection instrument is required, the cost of which is high. Moreover, since a radionuclide is used, there is a risk of nuclear pollution.

Therefore, it is important to develop a safe and effective lymphatic tracer for tracing SLN in a breast cancer operation, which predicts whether tumor metastasis occurs, so as to improve the quality of life of the patients with breast cancer and prolong lifetime of the patients.

SUMMARY

Based on the lymphatic system tropism of mitoxantrone, i.e., mitoxantrone stains lymph nodes near a tumor dark blue (the color of mitoxantrone), the present disclosure develops mitoxantrone as a lymphatic tracer for staining lymph nodes near the tumor in a breast cancer operation, which helps clinical positioning and dissection of lymph nodes.

Therefore, the present disclosure is directed to provide a use of mitoxantrone and/or a pharmaceutically acceptable salt thereof in preparation of a lymphatic tracer for a disease related to mastectomy.

In the present disclosure, unless otherwise specified, the scientific and technical terms used herein have the meanings commonly understood by those skilled in the art. Furthermore, the terms and experimental procedures related to protein and nucleic acid chemistry, molecular biology, cell and tissue culture, microbiology, and immunology that are used herein are all terms and conventional procedures widely used in corresponding fields. Meanwhile, in order to understand the present disclosure better, definitions and descriptions of related terms are provided below.

It is also to be understood that the terms used herein are only for the purpose of describing specific embodiments and are not intended to limit the present disclosure.

As used herein, the terms "patient", "individual", and "subject" are interchangeable, and refer to any single animal that desires treatment, more preferably, a mammal (including, for example, non-human animals, such as cats, dogs, horses, rabbits, zoo animals, cows, pigs, sheep, and non-human primates). In specific embodiments, the patient herein is a human. The patient has, is suspected of having or is at risk of having breast tumor. As used herein, the term "disease" refers to any condition that would benefit from treatment, which includes, but is not limited to, chronic and acute diseases or disorders, including those pathological conditions that predispose a mammal to the disease discussed.

As used herein, the term "pharmaceutical preparation" refers to a preparation in a form that allows the biological activity of an active ingredient contained therein to be effective, which does not contain other components that would have unacceptable toxicity to a subject to whom the preparation is administered.

As used herein, the term "pH regulator" refers to a compound or a mixture of multiple compounds for ensuring a pH value of a reconstruction kit to be within an acceptable administration range (a pH value of about 4.0 to 10.5) for humans or mammals. Suitable pH regulators include pharmaceutically acceptable buffers, such as tris(hydroxymethyl)methylglycine (tricine), phosphates, or tris(hydroxymethyl)aminomethane (TRIS); pharmaceutically acceptable acids, such as pharmaceutically acceptable organic acids (e.g., formic acid and acetic acid) or mixtures thereof, or inorganic acids (e.g., hydrochloric acid and phosphoric acid) or mixtures thereof, and pharmaceutically acceptable bases, such as sodium carbonate, sodium bicarbonate, or mixtures thereof. If a used conjugate is in a form of acidic salt, the pH regulator is optionally provided in a separate vial or container, such that a user for the kit may regulate the pH as part of a multi-step procedure.

As used herein, the term "pharmaceutically acceptable excipient" refers to an ingredient rather than an active ingredient in the pharmaceutical preparation that is nontoxic to subjects. Pharmaceutically acceptable excipients include, but are not limited to, buffers, carriers, stabilizers, or preservatives.

As used herein, the term "pharmaceutically acceptable salt" refers to a salt that is not undesirable biologically or in other aspects. Pharmaceutically acceptable salts include acid and base addition salts. The phrase "pharmaceutically acceptable" means that the substance or the composition needs to be chemically and/or toxicologically compatible with other ingredients for forming a preparation and/or a mammal to which the preparation is administered.

As used herein, the term "pharmaceutically acceptable acid addition salt" refers to those pharmaceutically acceptable salts formed with inorganic and organic acids, the inorganic acids include, for example, hydrochloric acid, hydrobromic acid, sulfuric acid, nitric acid, carbonic acid, and phosphoric acid, and the organic acids are selected from aliphatic, cycloaliphatic, aromatic, araliphatic, heterocyclic, carboxylic, and sulfonic organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, pamoic acid, phenylacetic acid, methanesulfonic acid (methanesulfonate), ethanesulfonic acid, p-toluenesulfonic acid, and salicylic acid.

The term "pharmaceutically acceptable base addition salt" refers to those pharmaceutically acceptable salts formed with organic or inorganic bases. Examples of the acceptable inorganic bases include salts of sodium, potassium, ammonium, calcium, magnesium, iron, zinc, copper, manganese, and aluminum. Salts derived from the pharmaceutically acceptable organic nontoxic bases include salts of primary amines, secondary amines, tertiary amines, substituted amines (including naturally occurring substituted amines), and cyclic amines, and salts of basic ion exchange resins, such as salts of isopropylamine, trimethylamine, diethylamine, triethylamine, tripropylamine, ethanolamine, 2-diethylaminoethanol, trimethylamine, dicyclohexylamine, lysine, arginine, histidine, caffeine, procaine, hydrabamine, choline, betaine, ethylenediamine, glucosamine, methylglucamine, theobromine, purine, piperazine, piperidine, N-ethylpiperidine, and polyamine resins.

As used herein, the term "treatment" refers to clinical interventions that attempt to alter the natural course of disease in an individual being treated, and can be used for prophylaxis or in the course of a clinical pathology. Desirable therapeutic effects include, but are not limited to, preventing the occurrence or recurrence of diseases, attenuating symptoms, reducing any direct or indirect pathological consequence of diseases, preventing metastasis, slowing down the progression speed of diseases, relieving or attenuating morbid state, and relieving or improving prognosis.

As used herein, the term "administration" refers to a method for giving a certain dosage of a compound (e.g., a mitoxantrone hydrochloride injection) or a pharmaceutical composition (e.g., a pharmaceutical composition containing an inhibitor or an antagonist) to a subject (e.g., a patient). The compound or the pharmaceutical composition can be administered in any suitable manner, including parenteral administration, intrapulmonary administration, and intranasal administration. If the compound or the pharmaceutical composition is needed for local treatment, it can be intralesionally administered. Parenteral infusion includes, for example, intramuscular administration, intravenous administration, intra-arterial administration, intraperitoneal administration or subcutaneous administration. Drugs can be administered by any suitable routes, for example, by injecting, such as intravenous injecting or subcutaneous injecting, which is partially determined by whether the administration is transient or prolonged. Various administration regimens are contemplated herein, which include, but are not limited to, single administration, multiple administrations at different time points, bolus injecting administration, and pulse infusion.

As used herein, a full analysis set (FAS), a set of subjects according to the principle of intention to treat (ITT) refers to a data set consisting of subjects who participate in a trial, receive treatment, and have baseline therapeutic effect evaluations.

As used herein, a per protocol set (PPS) refers to all subgroups of treated people who have completed a trial and excluded serious protocol violations (referring to objects for study who violate inclusion criteria or exclusion criteria), which is a set of patients who meet inclusion criteria, do not meet exclusion criteria, and have completed therapeutic regimen.

The present disclosure provides a use of mitoxantrone and/or a pharmaceutically acceptable salt thereof in preparation of a lymphatic tracer for a disease related to mastectomy.

The present disclosure further provides a lymphatic tracing method for a disease related to mastectomy, which includes administering mitoxantrone and/or a pharmaceutically acceptable salt thereof to a subject, the mitoxantrone and/or the pharmaceutically acceptable salt thereof being used as a lymphatic tracer.

In some specific embodiments, the disease related to mastectomy is selected from breast tumor, breast cyst, breast fibroma, or breast tuberculosis.

In some specific embodiments, the breast tumor includes benign breast tumor and malignant breast tumor.

In some preferred embodiments, the malignant breast tumor is breast cancer.

In some specific embodiments, the lymphatic tracer is used for tracing the lymph in a breast cancer.

In some specific embodiments, the lymphatic tracer contains mitoxantrone and/or a pharmaceutically acceptable salt thereof and a pharmaceutically acceptable excipient.

In some specific embodiments, the pharmaceutically acceptable excipient includes, but is not limited to, a buffer, a carrier, a stabilizer, or a preservative.

In some preferred embodiments, the lymphatic tracer is an injection.

In some specific embodiments, the injection is in a form of solution, lyophilized powder, emulsion, liposome, nanoparticles, nanocrystals, microcrystals, microspheres or gel.

In some preferred embodiments, the solution is a sodium chloride injection or a glucose injection.

In some specific embodiments, the injection is administered subcutaneously, intramuscularly, and subserosally, preferably, subcutaneously or subserosally; preferably, the injection is administered locally; preferably, injecting sites are on the mammary gland and/or tissues and organs around the breast; preferably, the injection is administered at multiple sites; preferably, the concentration of the injection is 2-10 mg/mL; preferably, the volume of the injection is 0.1-3.0 mL, and more preferably, at least 0.1 mL of the injection at a concentration of 5 mg/mL is administered; and preferably, a total dosage does not exceed 3.0 mL.

In some specific embodiments, the pharmaceutically acceptable salt is those pharmaceutically acceptable salts formed by mitoxantrone with an inorganic acid and an organic acid.

In some preferred embodiments, the inorganic acid is, for example, hydrochloric acid, hydrobromic acid, sulfuric acid, nitric acid, carbonic acid or phosphoric acid.

In some preferred embodiments, the organic acid is selected from aliphatic, cycloaliphatic, aromatic, araliphatic, heterocyclic, carboxylic, and sulfonic organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, pamoic acid, phenylacetic acid, methanesulfonic acid (methanesulfonate), ethanesulfonic acid, p-toluenesulfonic acid, and salicylic acid.

In some preferred embodiments, the pharmaceutically acceptable salt is selected from mitoxantrone hydrochloride, mitoxantrone oxalate, mitoxantrone sulfate, mitoxantrone phosphate, mitoxantrone acetate, and mitoxantrone citrate, and more preferably, the pharmaceutically acceptable salt is mitoxantrone hydrochloride.

In some specific embodiments, the lymphatic tracer contains a pH regulator.

In some preferred embodiments, the pH regulator is one or more selected from the group consisting of hydrochloric acid, phosphoric acid, sulfuric acid, oxalic acid, acetic acid, and citric acid.

In some specific embodiments, the lymphatic tracer contains an antioxidant.

In some preferred embodiments, the antioxidant is one or more selected from the group consisting of sodium sulfite, sodium bisulfite, sodium pyrosulfite, sodium thiosulfate, and disodium edetate; and preferably, the antioxidant is sodium pyrosulfite or disodium edetate.

In some preferred embodiments, the lymphatic tracer contains mitoxantrone or a salt thereof, sodium chloride, acetic acid, sodium acetate, and sodium pyrosulfite, and more preferably, the lymphatic tracer further contains sodium sulfate.

In some preferred embodiments, the lymphatic tracer contains mitoxantrone or a salt thereof, sodium chloride, acetic acid, sodium acetate, and disodium edetate.

In some preferred embodiments, a pH value of the injection is in a range of 2.8-4.3.

In some preferred embodiments, the content of the mitoxantrone or mitoxantrone in the salt thereof is 1-15 mg/mL, preferably, 2-10 mg/mL, and more preferably, 2 mg/mL, 5 mg/mL or 10 mg/mL, in terms of weight by volume.

In some preferred embodiment, the content of the sodium chloride is 3-18 mg/mL, preferably, 4-16 mg/mL, and more preferably, 4 mg/mL, 8 mg/mL or 16 mg/mL, in terms of weight by volume.

In some preferred embodiments, the content of the acetic acid is 0.15-1 mg/mL, preferably, 0.23-0.92 mg/mL, and more preferably, 0.23 mg/mL, 0.46 mg/mL or 0.92 mg/mL, in terms of weight by volume.

In some preferred embodiments, the content of the sodium acetate is 0.03-0.15 mg/mL, preferably, 0.05-0.1 mg/mL, and more preferably, 0.05 mg/mL or 0.1 mg/mL, in terms of weight by volume.

In some preferred embodiments, the content of the antioxidant is 0.05-0.3 mg/mL, preferably, 0.8-0.12 mg/mL, and more preferably, 0.1 mg/mL, 0.2 mg/mL or 0.3 mg/mL, in terms of weight by volume.

In some preferred embodiments, the content of the sodium sulfate is 0.05-0.6 mg/mL, preferably, 0.15-0.45 mg/mL, and more preferably, 0.15 mg/mL, 0.3 mg/mL or 0.45 mg/mL, in terms of weight by volume.

In some preferred embodiments, the injection is prepared by the following method:

(1) weighing prescribed amounts of acetic acid, sodium acetate, sodium chloride, and disodium edetate, or weighing prescribed amounts of acetic acid, sodium acetate, sodium chloride, and sodium pyrosulfite, or weighing prescribed amounts of acetic acid, sodium acetate, sodium chloride, sodium pyrosulfite, and sodium sulfate, mixing them with a solvent, and dissolving them to obtain a mixed solution of excipients, preferably, the solvent being water for injecting, preferably, the excipients being dissolved by stirring; and (2) mixing the mixed solution of excipients obtained in the step (1) with prescribed amounts of mitoxantrone and/or a pharmaceutically acceptable salt thereof, preferably, the mitoxantrone and/or the pharmaceutically acceptable salt thereof being dissolved by stirring, preferably, the mitoxantrone and/or the pharmaceutically acceptable salt thereof being dissolved by stirring for 10-30 min.

In some specific embodiments, the injection is prepared by the following method:

(1) weighing prescribed amounts of acetic acid, sodium acetate, sodium chloride, and disodium edetate, or weighing prescribed amounts of acetic acid, sodium acetate, sodium chloride, and sodium pyrosulfite, or weighing prescribed amounts of acetic acid, sodium acetate, sodium chloride, sodium pyrosulfite, and sodium sulfate, adding the excipients to a prescribed amount of water for injecting, and dissolving the excipients by stirring to obtain a mixture of the excipients; and (2) adding a prescribed amount of mitoxantrone or a salt thereof into the mixture of the excipients obtained in the step (1), and dissolving the mitoxantrone or the salt thereof by stirring to obtain a mitoxantrone hydrochloride injection, preferably, the mitoxantrone or the salt thereof being dissolved by stirring for 10-30 min.

In some specific embodiments, the method further includes:

(3) filtering, preferably, finely filtering with 0.45 μm and 0.22 μm of filter membranes.

In some specific embodiments, the method further includes:

(4) bottling and filling with nitrogen gas, with 2 mL each, capping, and sterilizing at 121° C. for 15 min, a pH value being in a range of 2.8-4.3.

In some preferred embodiments, the injection is prepared into a specification of 2 mL:10 mg.

Mitoxantrone hydrochloride used to be an antineoplastic drug originally, and is mainly used for treating malignant lymphoma, breast cancer, and acute leukemia at present. Based on the lymphatic system tropism of mitoxantrone, i.e., mitoxantrone stains lymph nodes near a tumor dark blue (the color of mitoxantrone), the present disclosure develops mitoxantrone as a lymphatic tracer which is locally injected in a tumor operation to stain lymph nodes near a tumor, and helps clinical positioning and dissection of lymph nodes. By in-depth study on preclinical pharmacodynamics of mitoxantrone hydrochloride, it is found that this drug has high affinity to lymph nodes while being subcutaneously injected or subserosally injected, and can stain lymph nodes blue. Therefore, the present drug can be used as a lymphatic tracer, and provides a new treatment idea in complete eradication of breast cancer for patients with breast cancer.

DETAILED DESCRIPTION OF EMBODIMENTS

For purposes of clarity and conciseness of description, features are described herein as part of the same or separate embodiments. However, it is to be understood that the scope of the present disclosure may include some embodiments having combinations of all or some of the described features.

Example 1 Preparation of a Mitoxantrone Hydrochloride Injection According to Formula 1

| Raw materials and excipients | Usage amount | |
|---|---|---|
| | g | % |
| mitoxantrone hydrochloride | 11.64 | 0.582 |
| sodium chloride | 16.0 | 0.8 |
| acetic acid | 0.92 | 0.046 |
| sodium acetate | 0.10 | 0.005 |
| disodium edetate | 0.40 | 0.02 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.5.

Example 2 Preparation of a Mitoxantrone Hydrochloride Injection According to Formula 2

| Raw materials and excipients | Usage amount | |
|---|---|---|
| | g | % |
| mitoxantrone hydrochloride | 23.28 | 1.164 |
| sodium chloride | 32.0 | 1.6 |

-continued

| Raw materials and excipients | Usage amount | |
|---|---|---|
| | g | % |
| acetic acid | 1.84 | 0.092 |
| sodium acetate | 0.20 | 0.01 |
| sodium pyrosulfite | 0.40 | 0.02 |
| sodium sulfate | 0.60 | 0.03 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.4.

Example 3 Preparation of a Mitoxantrone Hydrochloride Injection According to Formula 3

| Raw materials and excipients | Usage amount | |
|---|---|---|
| | g | % |
| mitoxantrone hydrochloride | 2.91 | 0.1455 |
| sodium chloride | 16.0 | 0.8 |
| acetic acid | 0.92 | 0.046 |
| sodium acetate | 0.10 | 0.005 |
| disodium edetate | 0.40 | 0.02 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.6.

Example 4 Preparation of a Mitoxantrone Hydrochloride Injection According to Formula 4

| Raw materials and excipients | Usage amount | |
|---|---|---|
| | g | % |
| mitoxantrone hydrochloride | 11.64 | 0.582 |
| sodium chloride | 16.0 | 0.8 |
| acetic acid | 0.92 | 0.046 |
| sodium acetate | 0.10 | 0.005 |

-continued

| Raw materials and | Usage amount | |
|---|---|---|
| excipients | g | % |
| sodium pyrosulfite | 0.20 | 0.01 |
| sodium sulfate | 0.30 | 0.015 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.7.

Example 5 Preparation of a Mitoxantrone Hydrochloride Injection According to Formula 5

| Raw materials and | Usage amount | |
|---|---|---|
| excipients | g | % |
| mitoxantrone hydrochloride | 23.28 | 1.164 |
| sodium chloride | 16.0 | 0.8 |
| acetic acid | 0.92 | 0.046 |
| sodium acetate | 0.10 | 0.005 |
| sodium pyrosulfite | 0.40 | 0.020 |
| sodium sulfate | 0.90 | 0.045 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.6.

Example 6 Preparation of a Mitoxantrone Hydrochloride Injection According to Formula 6

| Raw materials and | Usage amount | |
|---|---|---|
| excipients | g | % |
| mitoxantrone hydrochloride | 23.28 | 1.164 |
| sodium chloride | 16.0 | 0.8 |
| acetic acid | 0.92 | 0.046 |
| sodium acetate | 0.10 | 0.005 |
| disodium edetate | 0.60 | 0.03 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.7.

Example 7 Preparation of a Mitoxantrone Hydrochloride Injection According to Formula 7

| Raw materials and | Usage amount | |
|---|---|---|
| excipients | g | % |
| mitoxantrone hydrochloride | 11.64 | 0.582 |
| sodium chloride | 8.0 | 0.4 |
| acetic acid | 0.46 | 0.023 |
| sodium acetate | 0.10 | 0.005 |
| sodium pyrosulfite | 0.40 | 0.020 |
| water for injecting (made up to) | 2,000 mL | — |

Prescribed amounts of sodium chloride, acetic acid, sodium acetate, and sodium pyrosulfite were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.9.

Example 8 Preparation of a Mitoxantrone Hydrochloride Injection According to Formula 8

| Raw materials and | Usage amount | |
|---|---|---|
| excipients | g | % |
| mitoxantrone hydrochloride | 5.82 | 0.291 |
| sodium chloride | 8.0 | 0.4 |
| acetic acid | 0.46 | 0.023 |
| sodium acetate | 0.10 | 0.005 |
| sodium pyrosulfite | 0.40 | 0.020 |
| sodium sulfate | 0.60 | 0.03 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.5.

Example 9 Studies on Pharmacokinetic and Pharmacodynamic Assay of a Mitoxantrone Hydrochloride Injection A target organ of a mitoxantrone hydrochloride injection for lymphatic tracing is a lymph node in the breast drainage area. When mitoxantrone hydrochloride is compounded with hydrochloric acid, a uniform acidic solution can be formed. After a mitoxantrone hydrochloride injection is administered to the tissues space, the pH of the microenvironment changes, and mitoxantrone hydrochloride will gradually precipitate into nanocrystals. The crystals prevent mitoxantrone hydrochloride from entering the blood circulation through capillaries. Due to high permeability of lymphatic capillaries, mitoxantrone hydrochloride can enter the lymphatic capillaries through endothelial cell space as well as pinocytosis and phagocytosis of endothelial cells, reach regional lymph nodes through lymphatic drainage and enrich in regional lymph nodes, and stay in the lymph nodes for a period of time, thereby achieving effects of staining and tracing of the lymph nodes.

In order to test the safety and efficacy of a mitoxantrone hydrochloride injection for lymphatic tracing in tracing of lesion-draining lymph nodes in a patient with breast cancer, and to test the tolerance and in vivo pharmacokinetics of the mitoxantrone hydrochloride injection for lymphatic tracing in the subject with breast cancer so as to determine a safe dose range, this example adopted a single-center, randomized, open, and blank-controlled trial design. After the breast was fully exposed, a mitoxantrone hydrochloride injection for lymphatic tracing at a concentration of 5 mg/mL was administered at multiple sites on the breast gland. According to the size of the breast, a total dose of the injection was 0.1-3.0 mL. The tolerance in human being and pharmacokinetics in subjects were tested group by group, and the efficacy of the investigational drug was observed at the same time.

Pharmacokinetic results: the mitoxantrone hydrochloride injection is rapidly absorbed after being peritumorally administered, and the peak is basically reached 15-30 min after injecting. Moreover, the drug is metabolized rapidly after entering the blood, and the drug in the plasma is almost completely metabolized 60 min, 120 min at most, after the administration. In addition, the plasma concentration after the administration generally shows a dose-dependent trend, plasma concentrations in different subjects in a low-dose group are all lower than the lower limit of quantification at various time points; plasma concentrations in various patients in medium- and high-dose groups are equal to or higher than the lower limit of quantification at up to 4 time points; and the detected maximum concentration is 79.4 ng/ml only, which is about 6.5 times lower than the maximum concentration of 510±206 ng/mL reported in a document for patients with acute leukemia having received mitoxantrone chemotherapy by infusion administration (10-12 mg/m$^2$/d). In the document, high-dose mitoxantrone chemotherapy is used for treating ovarian cancer, the maximum tolerated total dosage of mitoxantrone administered by intravenous bolus is 75 mg/m$^2$, and AUC at this dose is 560-1700 ng×h/mL, which is 10.7-32.5 times the maximum AUC (3143 ng×min/ml) in the present trial.

Example 10 Application of a Mitoxantrone Hydrochloride Injection for Lymphatic Tracing in an Operation for a Patient with Breast Cancer 1. Clinical Trial Design The trial adopted a single-center, positive, and self-controlled trial design. According to the principle of dose escalation, the tolerance and pharmacokinetics in subjects were tested by intraoperative injection group by group, and the efficacy of the investigational drug was observed at the same time. The trial was planned to select 12 to 24 patients with breast cancer. The patients were divided into 4 groups with 3-6 patients in each group, and 0.5 mL, 1.0 mL, 2.0 mL, and 3.0 mL of mitoxantrone hydrochloride injection at a concentration of 5 mg/mL were respectively administered to each patient in the groups. One breast of each subject was injected with 2 mCi of nuclide-labeled sulfur colloid into the glands around the tumor 12 to 24 h before the operation in the nuclear medicine department, and imaging data was obtained to determine positions and the number of SLNs. The other breast of each subject was injected with the mitoxantrone hydrochloride injection, and each subject received only one dose of the investigational drug. The safety of the investigational drug was observed, the optimal dose and use method of the investigational drug were explored, and the efficacy of the investigational drug was investigated at the same time.

Investigational drug: the mitoxantrone hydrochloride injection for lymphatic tracing was injected into the glands around the tumor with a skin test needle in the operation, and the injecting sites were the same as those of the contrast drug, and a total dosage was 0.5-3.0 mL. Contrast drug: each subject participating in the trial was injected with 2 mCi of nuclide-labeled sulfur colloid into the glands around the tumor 12-24 h before the operation in the nuclear medicine department.

The trial was planned to select 9-18 18-70-year-old female subjects with breast cancer. Actually, 10 subjects completed the trial.

Efficacy Evaluation

Primary Endpoint

Comparison of success rates of SLN tracing with the investigational drug and the contrast drug Success rate of SLN tracing=the total number of patients with successful SLN tracing/the total number of patients participating in a trial×100%

The successful SLN tracing with the investigational drug refers to that SLNs traced by the investigational drug are stained axillary lymph nodes and lymph nodes to which stained lymph vessels point.

The successful SLN tracing with the contrast drug refers to that SLNs recognized by the contrast (nuclide) tracer are lymph nodes with the maximum Gamma probe count and a count value 10 times or more than the background count.

Secondary Endpoint

The number of SLNs traced by the investigational drug and the contrast drug, the number of SLNs traced together by the two tracers, and the number of SLNs that were not traced by the two drugs but clinically suspected were recorded.

Pathological states of SLNs detected by the investigational drug or the contrast drug were recorded.

The local damage caused by the investigational drug or the contrast drug was recorded.

Safety and Tolerance Evaluations

All subjects using the investigational drug were included in the evaluation of safety, tolerance, and endpoint indicators. The safety evaluation of the clinical trial was carried out until 21±3 days after the operation was completed. The evaluation was carried out by comparing hospital examination results two weeks before the trial to postoperative laboratory test results according to the adverse event evaluation basis, i.e., NCI's Criteria for Adverse Events Version 4.03 (CTCAE 4.0.3). The relationship between grades of adverse events and the investigational drug was judged to determine the maximum tolerated dose and a safe dose range.

2. Efficacy Results of the Clinical Trial

The study shows that the success rate of SLN tracing with the mitoxantrone hydrochloride injection for lymphatic tracing is higher, and there is no significant difference between the mitoxantrone hydrochloride injection and the contrast nuclide-labeled sulfur colloid. The success rates of SLN tracing with the contrast drug and groups of the investigational drug at a dose of 0.5 mL or 2.0 mL are all 100%. However, the success rates of SLN tracing with the contrast drug and a group of the investigational drug at a dose of 1.0 mL are 75%, and by analyzing the subjects participating in the trial, macro-cancerometastasis is found in 1 subject in this dose group. The reason may be that a lesion is large enough to block lymph vessels, and lymph nodes detected by both of the investigational drug and the contrast drug are not traced, causing failed tracing in the subject. There is no significant difference between the number of SLNs traced by the investigational drug at each dose and the number of SLNs traced by the contrast drug, as well as the number of SLNs traced together by the two tracers. There is no significant difference between the number of SLNs that are not traced by the investigational drug at each dose but clinically suspected and the number of SLNs that are not traced by the contrast drug but clinically suspected. It was indicated that compared with the nuclide method, the test drug has a good lymph node tracing effect. Pathological results of SLNs detected by the investigational drug and the contrast drug show that no cancerometastasis is found in SLNs traced by the investigational drug and the contrast drug.

Example 11 Application Case of a Mitoxantrone Hydrochloride Injection for Lymphatic Tracing in a Patient with Left Breast Cancer Preoperative diagnosis: right breast cancer (cT1N0M0)
Postoperative diagnosis: right breast cancer (sT1N0M0)
Operation name: total mastectomy for right breast+SLN labelling+effusion drainage×2
Intraoperative findings: when the right axilla is explored, six intumescent lymph nodes are seen, among which lymph nodes A, B, C, and D are stained blue and have nuclides, and lymph nodes E and F are not stained blue and do not have nuclides.

Operative procedures are as follows. The patient was placed in the supine position with the right upper limb abducing. After the general anesthesia took effect, 1.5 mL of drug at a concentration of 2 mL:10 mg was injected at 4 sites around the tumor, and the surgery field was conventionally disinfected and draped. Preoperative biopsy results of the patient showed a clear diagnosis of right breast cancer. A transverse incision with a length of about 10.0 cm was formed on the right chest wall, the skin flap was dissociated up to the subclavian area, down to the costal arch, laterally to the posterior axillary line, and medially to the midline.

The right entire breast, the surrounding adipose tissue, and the pectoralis major fascia were cut and removed. When the right axilla was explored, six intumescent lymph nodes were seen, among which lymph nodes A, B, C, and D were stained blue and had nuclides, and lymph nodes E and F were not stained blue and did not have nuclides. The lymph nodes were subjected to frozen pathology examination, and a pathological report (right breast SLNs A, B, C, D, E, and F) was obtained after 30 min and showed that no cancerometastasis was found in frozen lymph node slices. The wound was rinsed, after no active bleeding was found, the numbers of instruments and gauzes were checked, one drain was respectively placed at the axilla and the chest wall, and the incision was sutured. The operation was completed smoothly, anesthesia was appropriate, and the patient was transferred to the ward after operation.

Pathological examination results: (right breast SLNs A, B, C, D, E, and F) no cancerometastasis is found in frozen lymph node slices.

A total of 6 lymph nodes are detected, among which 4 lymph nodes are stained.

The invention claimed is:

1. A lymphatic tracing method for a disease related to mastectomy, comprising: administering a lymphatic tracer intraoperatively to a patient during mastectomy surgery,
   wherein the lymphatic tracer contains mitoxantrone hydrochloride, sodium chloride, acetic acid, sodium acetate, sodium pyrosulfite and sodium sulfate;
   wherein the content of the mitoxantrone hydrochloride is 1-15 mg/mL; the content of the sodium chloride is 3-18 mg/mL; the content of the acetic acid is 0.15-1 mg/ml; the content of the sodium acetate is 0.03-0.15 mg/mL; the content of the sodium pyrosulfite is 0.05-0.3 mg/mL; and the content of the sodium sulfate is 0.05-0.6 mg/ml,
   wherein the lymphatic tracer is an injection;
   wherein the injection is administered subcutaneously;
   wherein the injection is administered locally;
   wherein the injecting sites are on the breast gland and/or tissues and organs around the breast;
   wherein the injection is administered at multiple sites;
   wherein the concentration of the injection is 2-10 mg/ml; and
   wherein the volume of the injection is 0.1-3.0 mL.

2. The method according to claim 1, wherein the disease related to mastectomy is selected from breast tumor, breast cyst, breast fibroma, and breast tuberculosis.

3. The method according to claim 2, wherein the breast tumor is a benign breast tumor or a malignant breast tumor.

4. The method according to claim 3, wherein the malignant breast tumor is breast cancer.

5. The method according to claim 1, wherein
   at least 0.1 mL of the injection at a concentration of 5 mg/mL is administered; and a total dosage does not exceed 3.0 mL.

6. The method according to claim 1, wherein
   a pH value of the injection is in a range of 2.8-4.3;
   wherein the content of the mitoxantrone hydrochloride is 2-10 mg/mL, in terms of weight by volume;
   wherein the content of the sodium chloride is 4-16 mg/mL, in terms of weight by volume;
   wherein the content of the acetic acid is 0.23-0.92 mg/ml, in terms of weight by volume;
   wherein the content of the sodium acetate is 0.05-0.1 mg/mL, in terms of weight by volume;
   wherein the content of the sodium pyrosulfite is 0.8-0.12 mg/mL, in terms of weight by volume; and wherein the content of the sodium sulfate is 0.15-0.45 mg/mL, in terms of weight by volume.

7. The method according to claim 6, wherein the content of the mitoxantrone hydrochloride is 2 mg/mL, 5 mg/mL or 10 mg/mL, in terms of weight by volume;

the content of the sodium chloride is 4 mg/mL, 8 mg/mL or 16 mg/mL, in terms of weight by volume;

the content of the acetic acid is 0.23 mg/mL, 0.46 mg/mL or 0.92 mg/mL, in terms of weight by volume;

the content of the sodium acetate is 0.05 mg/mL or 0.1 mg/mL, in terms of weight by volume;

the content of the sodium pyrosulfite is 0.1 mg/mL, 0.2 mg/mL or 0.3 mg/mL, in terms of weight by volume;

the content of the sodium sulfate is 0.15 mg/mL, 0.3 mg/mL or 0.45 mg/mL, in terms of weight by volume.

* * * * *